United States Patent [19]
Yoon

[11] Patent Number: 5,380,321
[45] Date of Patent: Jan. 10, 1995

[54] SHIELDED ENERGY TRANSMITTING SURGICAL INSTRUMENT AND METHODS THEREFOR

[76] Inventor: InBae Yoon, 2101 Highland Ridge Dr., Phoenix, Md. 21131

[21] Appl. No.: 971,173

[22] Filed: Nov. 4, 1992

[51] Int. Cl.[6] .............................................. A61B 17/36
[52] U.S. Cl. ........................................ 606/41; 606/46; 606/49
[58] Field of Search ........................ 606/41–50, 606/13–16; 604/198; 607/98–102, 115, 116, 154–156; 128/642

[56] References Cited

U.S. PATENT DOCUMENTS

| | | | |
|---|---|---|---|
| 1,731,627 | 10/1929 | Johnson et al. | 606/50 |
| 4,043,342 | 8/1977 | Morrison, Jr. | 606/48 |
| 4,313,431 | 2/1982 | Frank | 606/14 |
| 4,900,311 | 2/1990 | Stern et al. | 604/198 |
| 4,919,129 | 4/1990 | Weber, Jr. et al. | 606/42 |
| 5,100,402 | 3/1992 | Fan | 606/41 |
| 5,193,526 | 3/1993 | Daikuzono | 606/7 |
| 5,197,963 | 3/1993 | Parins | 606/41 |

*Primary Examiner*—Stephen C. Pellegrino
*Assistant Examiner*—Michael Peffley

[57] ABSTRACT

A shielded energy transmitting surgical instrument for treating anatomical tissue with energy includes an energy transmitting member having a distal end for contacting tissue to be treated, a shield for shielding the distal end of the energy transmitting member and a hub mounting the energy transmitting member and the shield. The shield is movable, automatically in response to a force from tissue contact or manually, between an extended position protecting the distal end of the energy transmitting member and a retracted position wherein the distal end of the energy transmitting member is exposed for contact with the tissue. A source of energy supplies energy to the distal end of the energy transmitting member to treat the tissue, and the shield is movable thereafter toward the extended position to remove tissue from and protect the distal end of the energy transmitting member. A method of treating anatomical tissue with energy incudes the steps of moving the shield of the energy transmitting surgical instrument from the extended position to the retracted position to expose the distal end of the energy transmitting member, positioning the distal end of the energy transmitting member adjacent tissue to be treated, transmitting energy to the distal end of the energy transmitting member to treat the tissue and moving the shield to the extended position to remove tissue from and protect the distal end of the energy transmitting member.

5 Claims, 3 Drawing Sheets

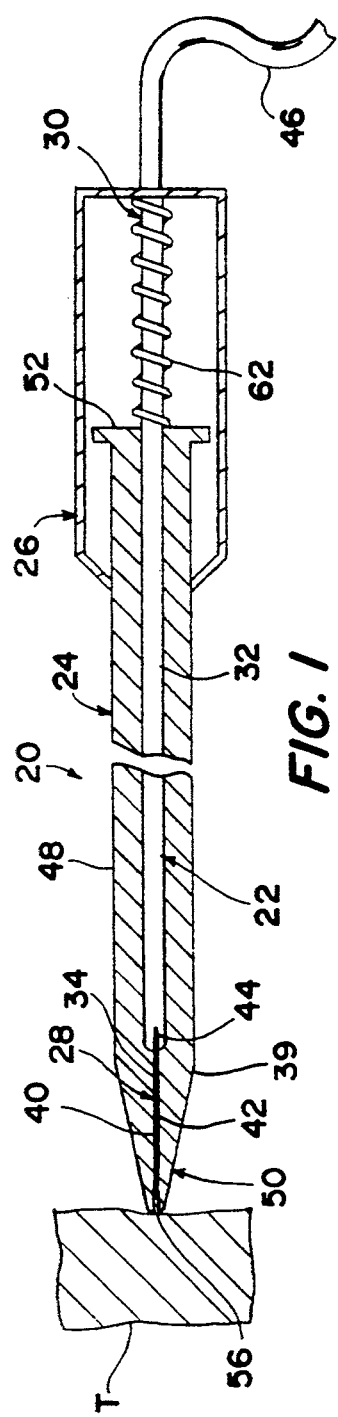
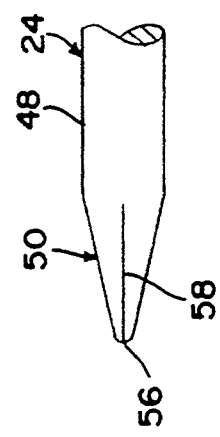
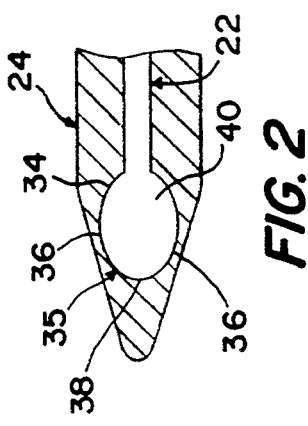
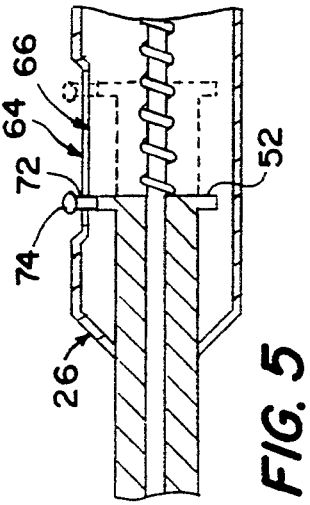

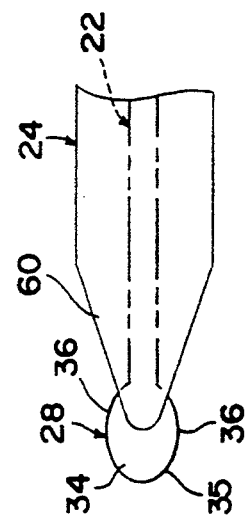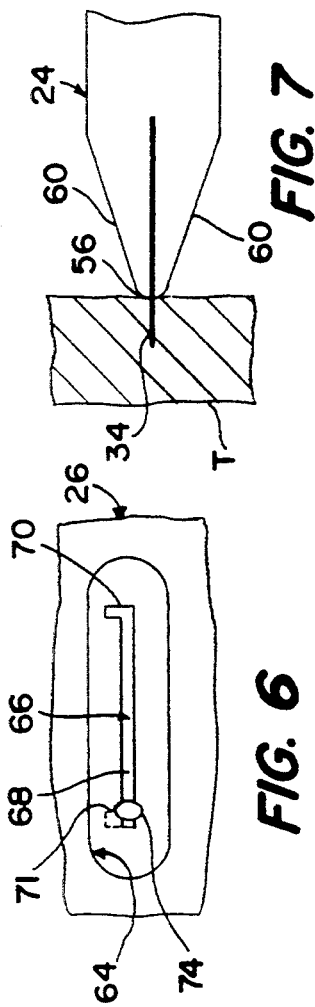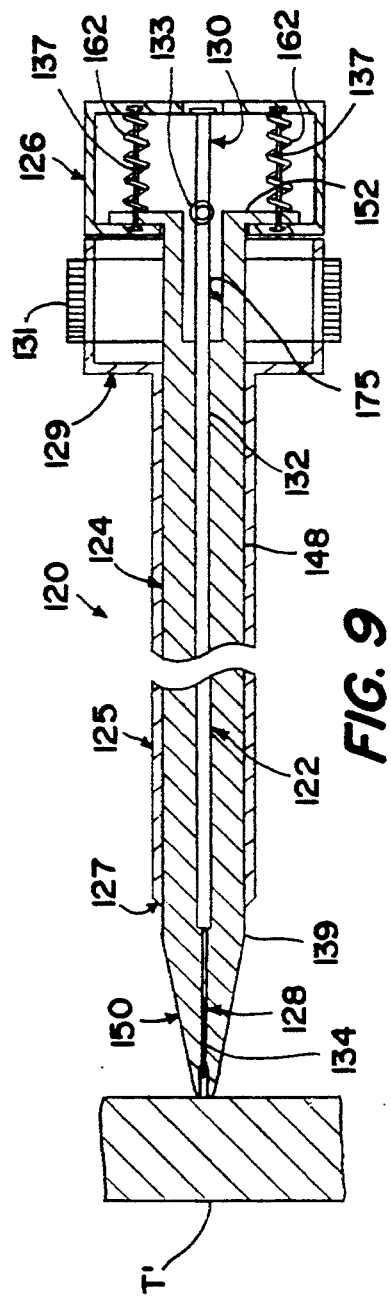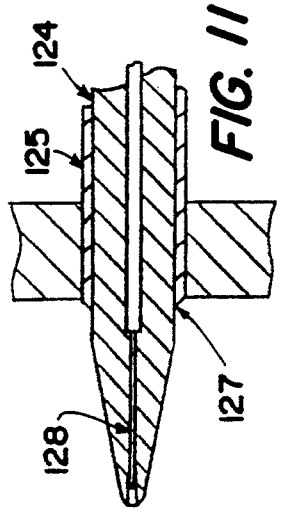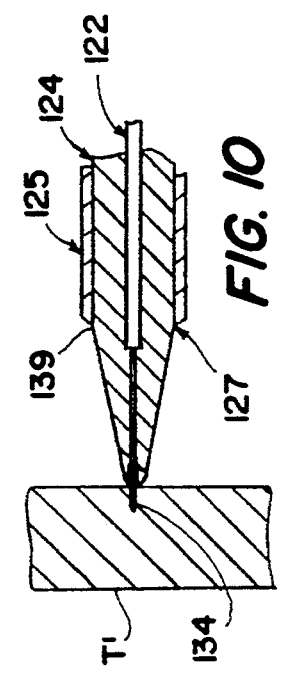

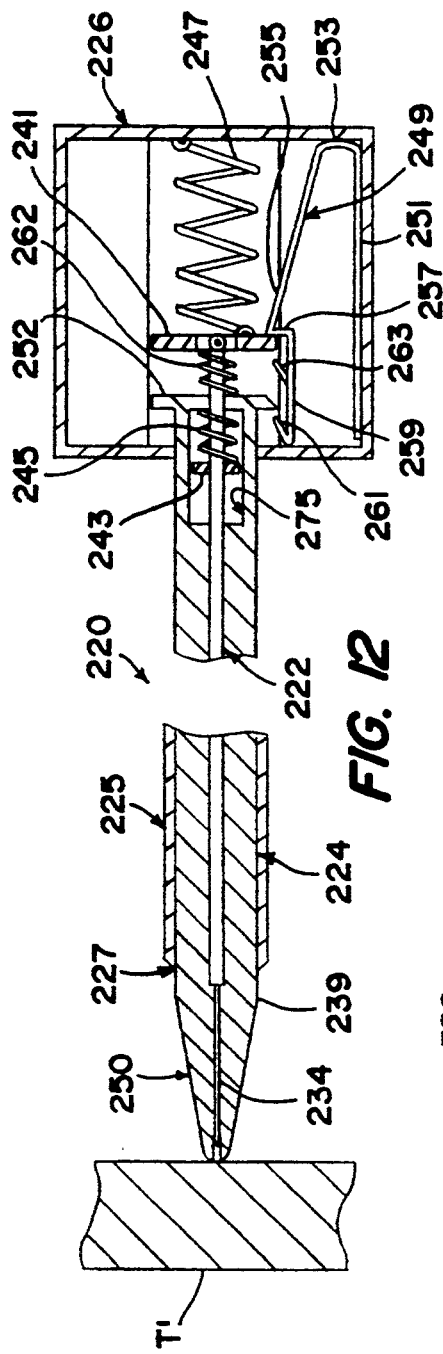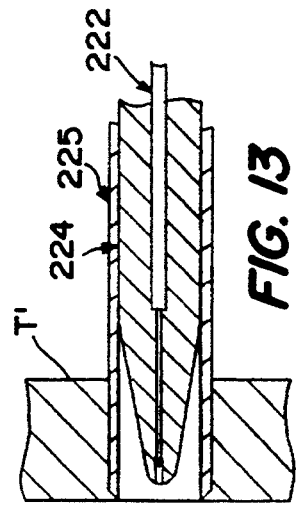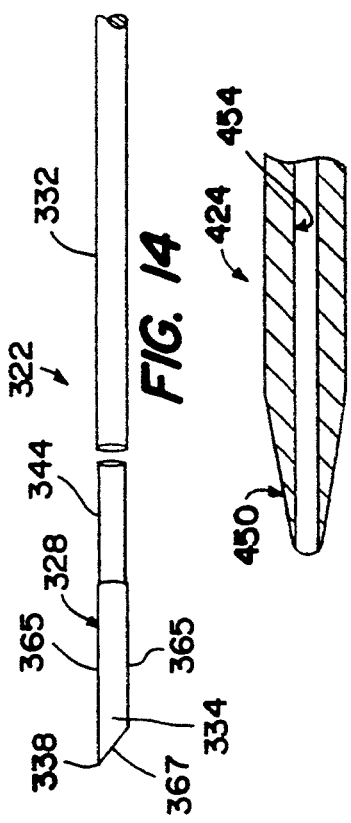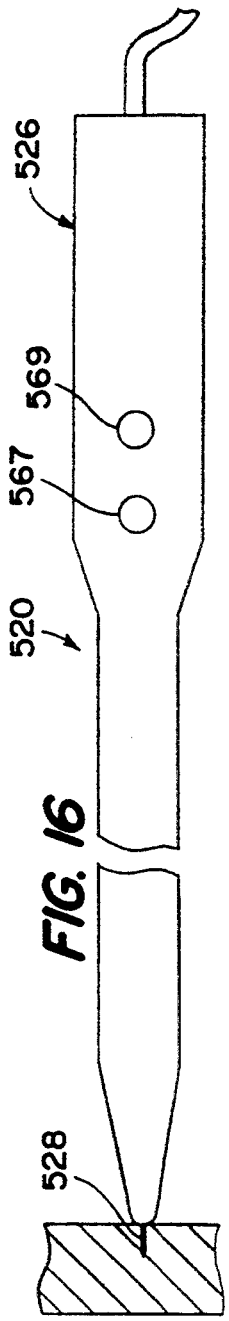

SHIELDED ENERGY TRANSMITTING SURGICAL INSTRUMENT AND METHODS THEREFOR

BACKGROUND OF THE INVENTION

1. Field of the Invention

The present invention pertains to surgical instruments for transmitting energy to tissue for cautery and coagulation and, in particular, to energy transmitting surgical instruments particularly useful in endoscopic surgery and methods therefor.

2. Description of the Prior Art

Closed, or endoscopic, surgery, otherwise known as least invasive surgery, has become extremely desirable for use in many fields including the laparoscopic, genito-urinary, spinal, breast, brain, thoracic and orthopedic fields. In endoscopic surgery, a portal sleeve is introduced into a cavity of the body through a portal of minimal size formed in a wall of the cavity. Once introduced, the portal sleeve can be utilized to introduce various surgical instruments into the cavity for various surgical procedures. One procedure which it is desirable to perform endoscopically is that of treating tissue with energy, such as electric or light energy, transmitted to the tissue by an energy transmitting member for cauterization and coagulation as well as other treatment procedures. U.S. Pat. No. 5,100,402 to Fan is illustrative of an instrument and method for electro-surgical laparoscopic cauterization. A disadvantage of prior art instruments and methods for treating tissue with energy endoscopically is that the energy transmitting member is not protected such that inadvertent contact with and destruction of healthy tissue can occur. Another disadvantage of prior art instruments and methods for treating tissue with energy endoscopically is that tissue can become stuck to the energy transmitting member such that the treatment procedure is impaired due to tissue trauma and the need to clean the energy transmitting member. A further drawback to prior art instruments and methods for endoscopically treating tissue with energy is that a single instrument cannot be utilized to both penetrate a wall of an anatomical cavity to introduce a portal sleeve therein and to treat tissue with energy following penetration of the cavity.

SUMMARY OF THE INVENTION

Accordingly, it is a primary object of the present invention to overcome the above mentioned disadvantages of prior art instruments and methods of treating tissue with energy endoscopically.

Another object of the present invention is to provide an energy transmitting surgical instrument having a shield for protecting an energy transmitting member of the instrument such that contact with the energy transmitting member can be prevented.

A further object of the present invention is to provide a shielded energy transmitting surgical instrument wherein the shield is movable between an extended position protecting a distal end of the energy transmitting member and a retracted position wherein the distal end of the energy transmitting member is exposed.

It is also an object of the present invention to provide a shielded energy transmitting surgical instrument wherein the shield is movable automatically from an extended position disposed beyond a distal end of the energy transmitting member to a retracted position wherein the distal end of the energy transmitting member is exposed in response to a force from tissue contact at a distal end of the instrument.

An additional object of the present invention is to provide a shielded energy transmitting surgical instrument wherein the shield is movable manually from an extended position protecting the distal end of the energy transmitting member to a retracted position exposing the distal end of the energy transmitting member to allow contact with tissue to be treated.

Yet another object of the present invention is to provide an energy transmitting surgical instrument with a shield for wiping the distal end of the energy transmitting member free of tissue upon movement of the shield between the retracted and extended positions.

A still further object of the present invention is to provide a shielded energy transmitting surgical instrument having an energy transmitting member for penetrating a wall of an anatomical cavity to position a portal sleeve therein and a shield movable to an extended position protecting the energy transmitting member in response to introduction of the portal sleeve into the cavity and movable thereafter to a retracted position to expose the energy transmitting member to treat tissue within the cavity.

The invention has as an additional object to provide a shielded energy transmitting surgical instrument for penetrating a wall of an anatomical cavity to introduce a portal sleeve therein wherein a distal end of the energy transmitting member and a distal end of the shield are automatically retracted within the portal sleeve in response to the portal sleeve entering the anatomical cavity.

It is also an object of the present invention to provide a method of treating tissue with energy including the steps of moving a shield of an energy transmitting surgical instrument to expose an energy transmitting member, contacting tissue to be treated with the energy transmitting member and moving the shield to an extended position to prevent contact with the energy transmitting member.

A further object of the present invention is to provide a method of treating tissue with energy including the step of removing tissue from an energy transmitting member in response to movement of a shield from a retracted position exposing the energy transmitting member toward an extended position protecting the energy transmitting member.

Yet another object of the present invention is to provide a method of treating tissue with energy endoscopically including the steps of moving a shield of an energy transmitting surgical instrument to expose a distal end of an energy transmitting member in response to forcing the instrument against a cavity wall, penetrating the wall with the energy transmitting member to position a portal sleeve within the cavity, moving the shield to protect the distal end of the energy transmitting member in response to introduction of the portal sleeve into the cavity and treating tissue within the cavity with the distal end of the energy transmitting member.

An additional object of the present invention is to provide a method of treating tissue with energy endoscopically including the steps of automatically retracting a distal end of a shield and a distal end of an energy transmitting member of an energy transmitting surgical instrument within a portal sleeve of the instrument upon positioning of the portal sleeve in an anatomical cavity with penetration into the cavity by the energy transmitting member and treating tissue within the cavity with the distal end of the energy transmitting member.

These and other objects, benefits and advantages are obtained with the present invention as characterized in a shielded energy transmitting surgical instrument including an energy transmitting member, a shield disposed around the energy transmitting member and a hub mounting the energy transmitting member and the shield. The energy transmitting member includes a distal end for contacting anatomical tissue to be treated and is connected with a source of energy, such as electrical or light energy, to be supplied to or through the energy transmitting member to the distal end thereof to treat the anatomical tissue. The shield is disposed around the energy transmitting member and is movable, automatically in response to a force from tissue contact at a distal end of the shield or manually, from an extended position wherein a distal end of the energy transmitting member is disposed within the shield in a safe, protected condition to a retracted position wherein the distal end of the energy transmitting member is disposed beyond the distal end of the shield to be exposed for contacting the tissue to be treated. With the shield in the retracted position, energy from the energy source is supplied to the distal end of the energy transmitting member to treat the tissue such as for cauterization and coagulation. Once the tissue has been treated, the shield is movable automatically or manually to the extended position with the shield moving along the distal end of the energy transmitting member to remove tissue therefrom. Where utilized to introduce a portal sleeve into an anatomical cavity, the instrument includes a portal sleeve disposed around the shield, the shield is biased to the extended position wherein the shield is disposed beyond a distal end of the portal sleeve and the distal end of the energy transmitting member is configured to penetrate tissue forming a wall of the anatomical cavity. When the instrument is forced against the cavity wall, the shield is moved automatically to the retracted position allowing penetration into the cavity by the energy transmitting member to position the distal end of the portal sleeve therein. Once the portal sleeve is positioned within the cavity, the shield automatically returns to the extended position allowing the instrument to be used to treat tissue within the cavity with energy. A method of treating tissue with energy according to the present invention includes the steps of moving a shield of an energy transmitting surgical instrument to expose an energy transmitting member, contacting tissue to be treated with the energy transmitting member and moving the shield to an extended position to prevent contact with the energy transmitting member.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 1 is a broken side view, partly in section, of a shielded energy transmitting surgical instrument according to the present invention.

FIG. 2 is a broken top view, partly in section, of the shielded energy transmitting surgical instrument of FIG. 1.

FIG. 3 is a broken side view of the shield for the shielded energy transmitting surgical instrument of FIG. 1.

FIG. 4 is a broken, side sectional view of the shield for the shielded energy transmitting surgical instrument of FIG. 1. FIG. 5 is a broken sectional view of the hub for the shielded energy transmitting surgical instrument of FIG. 1.

FIG. 6 is a broken view of the hub for the shielded energy transmitting surgical instrument of FIG. 1.

FIG. 7 is a broken side view of the shielded energy transmitting surgical instrument of FIG. 1 with the shield in a retracted position during application of energy to tissue.

FIG. 8 is a broken top view of the shielded energy transmitting surgical instrument of FIG. 1 with the shield in the retracted position.

FIG. 9 is a broken side view, partly in section, of a modification of the shielded energy transmitting surgical instrument according to the present invention.

FIG. 10 is a broken side view, partly in section, of the shielded energy transmitting surgical instrument of FIG. 9 during penetration of a wall of an anatomical cavity.

FIG. 11 is a broken side view, partly in section, of the shielded energy transmitting surgical instrument of FIG. 9 upon positioning of a portal sleeve in the anatomical cavity.

FIG. 12 is a broken side view, partly in section, of another modification of the shielded energy transmitting surgical instrument according to the present invention.

FIG. 13 is a broken side view, partly in section, of the shielded energy transmitting surgical instrument of FIG. 12 upon positioning of the portal sleeve in an anatomical cavity.

FIG. 14 is a broken side view of a modification of an energy transmitting member for the shielded energy transmitting surgical instruments according to the present invention.

FIG. 15 is a broken, side sectional view of a modification of a shield for use with the energy transmitting member of FIG. 14.

FIG. 16 is a broken side view of a further modification of a shielded energy transmitting surgical instrument according to the present invention.

DESCRIPTION OF THE PREFERRED EMBODIMENTS

A shielded energy transmitting surgical instrument according to the present invention is illustrated in FIG. 1 at 20 and includes an energy transmitting member 22, a shield 24 disposed around the energy transmitting member 22 and a hub 26 mounting energy transmitting member 22 and shield 24. Energy transmitting member 22 is in the nature of a probe, rod or electrode terminating distally at a distal end 28 and proximally at a proximal end 30 secured in hub 26. Energy transmitting member 22 includes a body 32 which can be flat with a uniform or non-uniform width and thickness, cylindrical or any other desired configuration in cross-section terminating distally at distal end 28 and proximally at proximal end 30. Body 32 has a length dependent on the location of anatomical tissue to be treated to position distal end 28 in contact with the tissue with the hub 26 held by the hand of a surgeon. For endoscopic use, body 32 is elongate allowing distal end 28 to be positioned in contact with tissue in the body while the hub 26 is secured, externally of the body, via the hand of the surgeon. Distal end 28 can have various configurations to be blunt or sharp; and, as illustrated in FIG. 1, distal end 28 is configured as a blade 34 for penetrating or cutting anatomical tissue. Where configured as a blade, distal end 28 can have various configurations to define a sharp edge for penetrating, cutting or dissecting tissue. As illustrated in FIG. 2, blade 34 includes a peripheral cutting edge 35 made up of opposing lateral cutting edge segments 36 terminating distally at a tip 38. The lateral cutting edge segments 36 can be arranged symmetrical with a longitudinal axis of the energy transmitting member with tip 38 aligned with the axis as illustrated in FIG. 2, or the cutting edge segments 36 can be non-symmetrical with the axis. The blade 34 has flat or planar anterior and posterior surfaces 40 and 42 with a minimal thickness therebetween to produce a narrow width cut or wound when penetrating tissue, and the anterior and posterior surfaces can be parallel as shown in FIG. 1 or non-parallel. The distal end 28 can be made separately from body 32 and mounted thereon in many various ways or the distal end can be made integrally, unitarily with the body 32. As shown in FIG. 1, distal end 28 is made separately from body 32, the blade 34 having a shank 44 extending proximally therefrom to be received in a slot or recess in body 32. Body 32 can have a thickness, outer diameter or size greater than the thickness of blade 34 to provide strength and rigidity to energy transmitting member 22 as shown in FIG. 1. Proximal end 30 can be secured in hub 26 in many various ways to be permanently or removably mounted therein. As illustrated in FIG. 1, proximal end 30 is secured along a rear wall of the hub 26 to be connected with a source of energy such as electric cable 46. Energy transmitting member 22 can be made of any suitable material to be inserted in the body in accordance with the form of energy to be transmitted by distal end 28. Where used to transmit electric energy, member 22 can be made of an electrically conductive material such as stainless steel.

Shield 24 includes a body 48 which can be cylindrical or have any other desired configuration in cross-section terminating distally at a distal end 50 and proximally at an end flange 52 disposed in hub 26. Body 48 for shield 24 surrounds or is concentrically disposed around the body 32 of the energy transmitting member and is cylindrical in cross-sectional configuration, the body 48 being tubular or formed with an internal passage 54 configured to receive the outer diameter or size of body 32. The length of body 48 is selected in accordance with the length of body 32 to position distal end 50 along distal end 28 in an extended position for the shield illustrated in FIG. 1. Distal end 50 of shield 24 can have various configurations to surround, receive, cover or protect the distal end 28 in the extended position such that contact with distal end 28 is prevented. Distal end 50 for shield 24 has a conical configuration and tapers distally from a cylindrical junction 39 joining the distal end 50 to the body 48 to a blunt or rounded end 56. Distal end 50 is split or bifurcated by a cut or slit 58 along a plane aligned with a longitudinal axis of the instrument 20 to define a pair of opposing fingers 60 disposed along the anterior and posterior surfaces 40 and 42 of the blade in the extended position. A bias member including a helical coil spring 62 is connected between the end flange 52 and a rear wall of hub 26 to bias the distal end 50 of shield 24 distally to the extended position, the spring 62 being disposed around the body 32 of the energy transmitting member. With the distal end 50 of shield 24 biased distally by spring 62, fingers 60 protrude laterally beyond the cutting edge segments 36 and distally beyond the tip 38 of blade 34 to shield the cutting edge 35 and prevent contact therewith. The shield 24 can be made of any suitable medical grade material for use in the body; and, where electrical energy is to be transmitted by the energy transmitting member 22, the shield can be made of electrically insulative material. Slit 58 can have various configurations to accommodate blade 34 in the extended position and body 32 when the distal end 50 is moved proximally relative to the distal end of the energy transmitting member to expose the energy transmitting member distal end 28, or the fingers can be made of a resilient, flexible or elastic material such as rubber to conform to the configuration of blade 34 in the extended position and body 32 when the distal end 50 of the shield is moved proximally relative to the distal end 28 of the energy transmitting member. Shield 24 can have an outer diameter or size to permit introduction of the instrument in an anatomical cavity through a portal sleeve accessing the cavity via a portal of minimal size formed in a wall of the cavity for endoscopic use being introduced.

Hub 26 can have any suitable configuration and can be made of any suitable material to be disposable or reusable; and, where electrical energy is to be transmitted by the energy transmitting member 22, the hub can be made of electrically insulative material. As illustrated in FIG. 1, hub 26 has a rectangular configuration with a tapered forward end to facilitate grasping by a surgeon. As best illustrated in FIGS. 5 and 6 a side wall of hub 26 has a central recessed channel 64 formed therein with a slot 66 formed in the hub wall within the recessed channel. The slot 66 is made up of a longitudinal slot portion 68 disposed parallel with the longitudinal axis of the instrument 20 and a proximal transverse slot portion 70. A pin 72 is secured to the shield 24, such as being threadedly secured along the periphery of end flange 52 as illustrated in FIG. 5, to be received within slot 66 and terminates at an external knob 74. The location of the transverse slot portion 70 corresponds to the position of pin 72 along longitudinal slot portion 68 when the shield 24 is in a retracted position as will be explained further below.

According to a method of operation for shielded energy transmitting surgical instrument 20, the instrument is normally provided in a rest state with spring 62 in a relaxed, unbiased or unloaded state and shield 24 in the extended position with distal end 28 of the energy transmitting member disposed within the shield 24 to be in a safe, protected condition with no parts of the energy transmitting member exposed as illustrated in FIG. 1. With the instrument in the extended position, pin 72 is disposed at a distal end of longitudinal slot portion 68, and fingers 60 of shield 24 protrude beyond and protect the cutting edge 35 of blade 34. When it is desired to utilize instrument 20 to treat anatomical tissue, end 56 of shield 24 is positioned against tissue to be treated, such as tissue T illustrated in FIG. 1, and the instrument is forced against the tissue. The resistance of the tissue T causes shield 24 to be moved proximally against the bias of spring 62 such that distal end 50 is moved proximally to a retracted position illustrated in FIGS. 7 and 8. With the shield 24 in the retracted position, distal end 28 of energy transmitting member 22 will be exposed allowing the energy transmitting member to be utilized to transmit energy to the tissue for cautery or coagulation. As illustrated in FIG. 8, movement of the shield 24 proximally causes the cutting edge 35 to be exposed allowing the blade to be utilized to penetrate, cut or dissect tissue incident to treatment with energy. By moving the blade in a direction aligned with the lateral cutting edge segments 36 with a side to side or rotational movement, the tissue can be controllably penetrated. Electrical energy, such as RF electrical energy, is transmitted along the energy transmitting member 22 via cable 46 in response to actuation of a button or switch provided on the instrument 20 or connected with the energy source. The electrical energy is transmitted to the tissue via contact of the tissue T with blade 34 in a unipolar or monopolar mode of operation to treat the tissue, such as to produce cautery or coagulation, in accordance with the frequency of energy transmitted to the tissue. Once the tissue has been treated, the instrument 20 is withdrawn or backed away from the tissue causing shield 24 to automatically return to the extended position protecting the distal end 28 of the energy transmitting member 22. Movement of the shield from the retracted position toward the extended position causes fingers 60 to move distally along the anterior and posterior surfaces 40 and 42 of blade 34, the fingers moving along the blade with a wiping action to clean or remove any tissue from the blade. Accordingly, the instrument is ready to be used for further treatment. By providing the energy transmitting member with both an active and passive electrode, the shielded energy transmitting instrument can be utilized for bipolar operation.

Instrument 20 can be operated manually without forcing the end of the shield against the tissue such that the distal end of the energy transmitting member does not need to penetrate the tissue. Knob 74 is grasped by the surgeon and moved proximally along longitudinal slot portion 68 causing proximal movement of shield distal end 50 to expose distal end 28 of the energy transmitting member. Knob 74 is moved laterally relative to the longitudinal slot portion 68 to position pin 72 in the transverse slot portion 70 thusly locking the shield in the retracted position. Distal end 28 is positioned in contact with anatomical tissue to be treated, and a source of energy, which can be electrical as previously described or light energy, is transmitted along the energy transmitting member to the tissue. Where light energy is utilized, the light energy can be transmitted via fiber optic cables for use of the energy transmitting member as a contact laser. Once the tissue has been treated, the pin 72 is moved via knob 74 into the longitudinal slot portion 68 allowing movement of shield 24 by spring 62 distally to the extended position. By providing a distal transverse slot portion 71 corresponding in location to the position of pin 72 along longitudinal slot portion 68 in the extended position, the shield 24 can be locked in the extended position as illustrated in FIG. 6 by moving the pin via knob 74 into the distal transverse slot portion. The distal transverse slot portion can extend from the longitudinal slot portion in the same direction as proximal transverse slot portion 70 as shown or in a direction opposite thereto.

A modification of the shielded energy transmitting surgical instrument according to the present invention is illustrated at 120 in FIG. 9, the instrument 120 being particularly useful in closed or endoscopic surgery to introduce a portal sleeve into an anatomical cavity. The instrument 120 is similar to instrument 20 except that the shield 124 for instrument 120 is disposed within a portal sleeve 125 to be introduced into an anatomical cavity. Portal sleeve 125 includes an elongate cylindrical body terminating distally at a distal end 127 and proximally at a proximal end secured in or formed with a front wall of a valve housing 129. Accordingly, the instrument 120 can be considered to be formed of a portal unit and a penetrating unit, the portal unit including portal sleeve 125 and valve housing 129 and the penetrating unit including energy transmitting member 122, shield 124 and hub 126 mounting energy transmitting member 122 and shield 124. The valve housing 129 has a rear wall with an opening therein allowing passage therethrough by the penetrating unit and an internal channel aligned with the lumen of portal sleeve 125 and the opening in the rear wall. A valve assembly 131, which can be of any type, is mounted in the valve housing to prevent fluid flow through the housing in a closed position for the valve assembly while allowing passage therethrough by the penetrating unit in an open position for the valve assembly as shown in FIG. 9. Accordingly, the penetrating unit is removable from the portal unit allowing the penetrating unit to be withdrawn from the portal unit leaving the portal sleeve in place within an anatomical cavity. Energy transmitting member 122 for instrument 120 is similar to energy transmitting member 22 except that a unipolar electrical or heat connector or a contact laser connector 133 extends through a side wall of hub 126 to be connected with the body 132 of the energy transmitting member 122 distally of proximal end 130. Shield 124 is similar to shield 24 except that a longitudinal recess 175 is disposed in a proximal end of the shield and terminates distally at an end wall allowing movement of the shield proximally by connector 133 to the retracted position. The bias member for instrument 120 is similar to the bias member for instrument 20 and includes a pair of helical coil springs 162 connected between end flange 152 and a rear wall of hub 126. If desired, guide rods 137 can extend between the rear wall of the hub and a front wall thereof with the springs 162 concentrically disposed around the guide rods to maintain axial alignment of the springs. Hub 126 is similar to hub 26 for instrument 20; however, the length of hub 126 is minimized or reduced compared to that for hub 26 to facilitate grasping of the hub and the valve housing by a surgeon with one hand.

According to a method of operation for shielded energy transmitting surgical instrument 120, the instrument 120 is normally provided in a rest state with springs 162 in relaxed, unloaded or unbiased states and shield 124 biased distally to the extended position with distal end 150 shielding the distal end 128 of energy transmitting member 122 as illustrated in FIG. 9. In the extended position, junction 139 joining distal end 150 to body 148 of the shield is disposed distally of the distal end 127 of the portal sleeve 125, as illustrated in FIG. 9 wherein the instrument is shown just prior to penetrating tissue T' forming a wall of an anatomical cavity. When it is desired to utilize instrument 120 to penetrate tissue T' and enter the anatomical cavity, the instrument is forced against the tissue as illustrated in FIG. 10 causing movement of distal end 150 of shield 124 proximally to the retracted position. With the shield in the retracted position, junction 139 will be substantially aligned with the distal end 127 of portal sleeve 125 to form a substantially smooth profile and blade 134 will be exposed allowing the instrument to be utilized to penetrate through the tissue T' with the shield 124 following through the tissue. By forming the distal end 150 to have a tapered configuration or a configuration complementary to the configuration of the distal end 128, penetration through the tissue is facilitated. Once the distal end 127 of the portal sleeve 125 has entered the anatomical cavity, shield 124 will be moved automatically to the extended position due to the bias of springs 162 such that the distal end 128 is once again in the safe, protected position. Movement of shield 124 to the extended position wipes the distal end 128 free of tissue such that the instrument is ready to be utilized to treat tissue within the anatomical cavity as described previously above for shielded energy transmitting instrument 20.

Another modification of a shielded energy transmitting surgical instrument according to the present invention is illustrated at 220 in FIG. 12. Shielded energy transmitting surgical instrument 220 is similar to instrument 120 and includes a penetrating unit for being combined with a portal unit to introduce a portal sleeve of the portal unit into an anatomical cavity. The penetrating unit for instrument 220 includes a shield 224 similar to shield 124 except that end flange 252 has an opening therein communicating with a longitudinal recess 275 formed in a proximal end of the shield, the opening in the end flange allowing passage therethrough by the energy transmitting member 222. Energy transmitting member 222 is similar to energy transmitting member 122 except that energy transmitting member 222 terminates proximally at a retracting mechanism including a retraction plate 241 disposed in hub 226. A bias member including a helical coil spring 262 is disposed concentrically around a proximal end of the energy transmitting member and is connected between the retraction plate 241 and the end flange 252 to bias the shield 224 in a distal direction. An external wall or shoulder 243 is carried on the body of the energy transmitting member to be disposed in recess 275, and a helical coil balancing or cushion spring 245 is disposed concentrically around the energy transmitting member 222. Cushion spring 245 is connected between end flange 252 and shoulder 243 to bias the shield 224 proximally against the distal bias of spring 262 such that the end flange 252 is disposed at an initial or balanced position with the shield in the extended position as illustrated in FIG. 12. The retracting mechanism includes retraction plate 241 and a retracting spring 247 disposed in hub 226 and connected between a rear wall of the hub and the retraction plate 241 to bias the energy transmitting member 222 in a proximal direction. A locking and releasing mechanism 249 is disposed in hub 226 and includes a latch or locking spring having a base 251 secured to a wall of the hub and terminating proximally at a bend 253, a locking arm 255 extending angularly, distally from the bend in the direction of a longitudinal axis of the instrument 220 and a bent locking member or finger 257 carried on arm 255 to be engaged with retraction plate 241 in a normal condition for the spring illustrated in FIG. 12. An extension 259 of arm 255 extends in a distal direction from locking finger 257 parallel with the instrument axis, and a trigger or release member 261 is carried on extension 259 to be disposed distally of end flange 252 in the initial position. An additional trigger or release member 263 is carried on extension 259 to be disposed proximally of end flange 252 in the initial position as illustrated in FIG. 12. Trigger 261 is angled from extension 259 in a proximal direction to be engaged by end flange 252 to cause flexing of arm 255 upon movement of the end flange distally of the initial position. Trigger 263 is similarly angled from extension 259 to allow movement of end flange 252 proximally thereby from the initial position to a set position without causing flexing of arm 255 and to be engaged by the end flange to cause flexing of arm 255 upon movement of the end flange distally from the set position toward the initial position. Springs 245 and 262 can be of equal strength to maintain the end flange 252 at the initial position; however, where end flange 252 abuts trigger 261 in the initial position, the cushion spring 245 can be of lesser strength than the spring 262 due to the increased resistance provided by the trigger 261.

Shielded energy transmitting surgical instrument 220 can be used to penetrate tissue and enter an anatomical cavity in a manner similar to that previously described for instrument 120. The penetrating unit is combined with the portal unit; and, with the shield 224 in the extended position, end flange 252 will be disposed in the initial position proximally of trigger 261 and distally of trigger 263 with the junction 239 of shield 224 disposed beyond the distal end 227 of the portal sleeve 225. With the shield in the extended position, the blade 234 of the energy transmitting member 222 will be shielded by the distal end 250 of the shield, and the locking spring will be in the normal condition with locking finger 257 engaged with retraction plate 241 to prevent proximal movement thereof. When it is desired to utilize the instrument 220 to penetrate tissue and enter an anatomical cavity, the instrument is forced against the tissue T', and the resistance of the tissue causes shield 224 to be moved proximally to the retracted position with the junction 239 substantially aligned with the distal end 227 of the portal sleeve as previously discussed for instrument 120. Movement of shield 224 to the retracted position causes end flange 252 to be moved proximally of the initial position to a set position disposed proximally of trigger 263, the end flange moving proximally by trigger 263 without causing bending of arm 255 such that the retraction plate 241 remains locked in place against locking finger 257. Once the distal end of portal sleeve 225 has entered the anatomical cavity, shield 224 will be moved distally toward the extended position due to the bias of spring 262, causing end flange 252 to engage trigger 263 and flex arm 255 in a direction outwardly from the instrument axis to release locking member 257 from engagement with retraction plate 241. Retracting spring 247 will automatically move the energy transmitting member in the proximal direction carrying with it the shield 224 via engagement of end flange 252 with spring 245. Accordingly, the distal ends of the shield 224 and the energy transmitting member 222 will be moved to a retracted position disposed within the portal sleeve such that no parts of the instrument extend beyond the distal end of the portal sleeve to protrude into the anatomical cavity. By providing a knob, such as on the retraction plate or the end flange, and a slot arrangement as previously described, the energy transmitting member 222 and the shield 224 can be manually moved distally to the rest position for use in treating tissue in the anatomical cavity as previously described. Use of a knob and slot arrangement also permits the shield to be locked in the extended position for use as a standard penetrating instrument. Where end flange 252 does not move far enough to the set position to move proximally by trigger 263 or where trigger 263 is not desired, trigger 261 can be utilized to actuate retraction of the energy transmitting member and the shield in that, once the distal end of the portal sleeve has been introduced into the anatomical cavity, end flange 252 will be moved distally from the set position with the momentum of the spring 262 causing the end flange to be moved distally of the initial position to engage trigger 261 and flex arm 255 to release the retraction plate. Various retracting and locking and releasing mechanisms can be utilized in the instrument 220 to actuate retraction including the various retracting and locking and releasing mechanisms disclosed in applicant's co-pending patent application Ser. No. 07/800,507, filed Nov. 27, 1991, Ser. No. 07/805,506, now U.S. Pat. No. 5,330,432, filed Dec. 6, 1991, Ser. No. 07/808,325, now U.S. Pat. No. 5,324,268, filed Dec. 16, 1991, and Ser. No. 07/848,838, filed Mar. 10, 1992, Ser. No. 07/868,566, now U.S. Pat. No. 5,320,610 filed Apr. 15, 1992, Ser. No. 07/868,578, now U.S. Pat. No. 5,336,176 filed Apr. 15, 1992 and Ser. No. 07/929,338, filed Aug. 14, 1992, the specifications of which are incorporated herein by reference.

A modification of an energy transmitting member for use with the shielded energy transmitting instrument of the present invention is illustrated at 322 in FIG. 14. Energy transmitting member 322 has a distal end 328 configured as a knife blade 334. Blade 334 is made up of opposing, straight lateral sides 365 and a straight forward cutting edge 367. One of the sides 365 is longer than the other, and the forward cutting edge 367 angularly joins the sides 365 with the cutting edge 367 terminating distally at a tip 338 adjacent the longer lateral side. Where desired, sides 365 can be sharpened along all or part of the length thereof to define opposing lateral cutting edge segments extending proximally from forward cutting edge 367. Energy transmitting member 322 has a body 332 which is cylindrical and tubular or partly tubular or formed with an internal passage to receive a shank 344 of blade 334. Body 332 has an outer diameter or size that is the same as the width of blade 334, the width being measured between sides 365 in a direction transverse or perpendicular to a longitudinal axis of the energy transmitting member 322.

A modification of a shield for the shielded energy transmitting surgical instrument of the present invention is illustrated in FIG. 15 at 424, the shield 424 being particularly useful with energy transmitting member 322. Shield 424 is similar to shield 24 except that the lumen or internal passage 454 for shield 424 has a diameter or size that is constant or uniform along the length of the shield 424. Passage 454 has a diameter or size to receive the outer diameter or size of energy transmitting member 322 to allow movement of the shield relative to the energy transmitting member between the extended and retracted positions.

Yet another modification of a shielded energy transmitting surgical instrument according to the present invention is illustrated at 520 in FIG. 16. Instrument 520 is similar to instrument 20 except that manually actuatable pushbuttons or switches 567 and 569 are provided externally along hub 526 for use in transmitting energy to distal end 528. Buttons or switches 567 and 569 correspond to different frequencies of electrical energy to be supplied to distal end 528 allowing selection of cautery or coagulation modes of operation in accordance with the different frequencies.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of treating anatomical tissue within an anatomical cavity including the steps of
forcing a distal end of an energy transmitting surgical instrument against a wall of the anatomical cavity;
moving a shield of the energy transmitting surgical instrument to expose a distal end of an energy transmitting member of the energy transmitting surgical instrument in response to resistance of the cavity wall;
penetrating the cavity wall with the distal end of the energy transmitting member to introduce a portal sleeve of the energy transmitting surgical instrument within the cavity;
shielding the distal end of the energy transmitting member in response to introduction of the portal sleeve into the anatomical cavity;
exposing the distal end of the energy transmitting member;
supplying energy to the distal end of the energy transmitting member; and
treating the tissue with the distal end of the energy transmitting member.

2. A method of treating anatomical tissue as recited in claim 1 wherein said step of shielding includes moving the shield to an extended position wherein the distal end of the energy transmitting member is disposed within the shield.

3. A method of treating anatomical tissue as recited in claim 1 wherein said step of shielding includes retracting a distal end of the shield and the distal end of the energy transmitting member within the portal sleeve.

4. A method of treating anatomical tissue as recited in claim 1 wherein said step of treating includes cauterizing the tissue.

5. A method of treating anatomical tissue as recited in claim 1 wherein said step of treating includes coagulation.

* * * * *